(12) United States Patent
Maruyama et al.

(10) Patent No.: US 8,741,134 B2
(45) Date of Patent: Jun. 3, 2014

(54) FRACTIONATING/COLLECTING DEVICE OF LIQUID CHROMATOGRAPH

(75) Inventors: Shuzo Maruyama, Kyoto (JP); Yosuke Iwata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 2376 days.

(21) Appl. No.: 11/311,166

(22) Filed: Dec. 20, 2005

(65) Prior Publication Data
US 2006/0091053 A1    May 4, 2006

Related U.S. Application Data

(62) Division of application No. 10/834,968, filed on Apr. 30, 2004, now Pat. No. 7,138,050.

(30) Foreign Application Priority Data

May 29, 2003 (JP) ................................. 2003-152611
May 29, 2003 (JP) ................................. 2003-152612

(51) Int. Cl.
B01D 15/08 (2006.01)
(52) U.S. Cl.
USPC .......... 210/198.2; 210/656; 210/659; 422/63; 422/64; 422/70
(58) Field of Classification Search
USPC .............. 210/198.2, 656, 659; 422/63, 64, 70
See application file for complete search history.

(56) References Cited

U.S. PATENT DOCUMENTS

| 4,476,733 | A |   | 10/1984 | Chlosta et al. |
| 4,591,442 | A | * | 5/1986  | Andrews ........................ 210/656 |
| 4,753,775 | A | * | 6/1988  | Ebersole et al. ................. 422/81 |
| 4,766,082 | A | * | 8/1988  | Marteau D'Autry ......... 436/178 |
| 5,091,092 | A | * | 2/1992  | Newhouse et al. ........... 210/635 |
| 5,100,557 | A | * | 3/1992  | Nogami et al. ................ 210/656 |
| 5,107,908 | A | * | 4/1992  | Newhouse et al. ........... 141/130 |
| 5,395,521 | A | * | 3/1995  | Jagadeeswaran .......... 210/198.2 |
| 6,060,022 | A | * | 5/2000  | Pang et al. ....................... 422/65 |
| 6,355,164 | B1 | * | 3/2002 | Wendell et al. ............. 210/198.2 |

(Continued)

FOREIGN PATENT DOCUMENTS

CN         2169985 Y      6/1994
JP       09-098797 A      4/1997

(Continued)

OTHER PUBLICATIONS

Chinese Office Action, Application No. 20410044674.8, dated Feb. 24, 2006.

*Primary Examiner* — Ernest G Therkorn
(74) *Attorney, Agent, or Firm* — Cheng Law Group, PLLC

(57) ABSTRACT

In a preferred embodiment, a sample container storage part for storing a number of sample containers S, a nozzle for dropping a sample component separated and supplied by an LC and an additive liquid such as digestive fluid supplied from another liquid supplying part to the sample container S, a carrying mechanism for carrying and positioning the sample container at an arbitrary position under the nozzle, and a second nozzle, serving as a suction/injection mechanism, for sucking in the fractionated/collected sample component and injecting the sample component to another LC. The carrying mechanism provides a rotation mechanism. The carrying mechanism rotates over 180 degrees and carries the sample container S completed with fractionating/collecting to the position of the second nozzle, and the sample is sucked in by the second nozzle and injected to the LC of next stage.

6 Claims, 3 Drawing Sheets

(56) References Cited

U.S. PATENT DOCUMENTS

| | | | |
|---|---|---|---|
| 6,360,589 B1 * | 3/2002 | Kanda et al. | 73/61.52 |
| 6,416,663 B1 * | 7/2002 | Miroslav et al. | 210/198.2 |
| 6,582,597 B2 * | 6/2003 | Hsi et al. | 210/198.2 |
| 6,586,257 B1 * | 7/2003 | Vuong | 436/165 |
| 6,620,625 B2 * | 9/2003 | Wolk et al. | 436/180 |
| 6,685,884 B2 * | 2/2004 | Stylli et al. | 422/63 |
| 6,787,030 B2 * | 9/2004 | Hsi et al. | 210/198.2 |
| 6,814,933 B2 * | 11/2004 | Vuong | 422/82.05 |
| 7,138,050 B2 * | 11/2006 | Maruyama et al. | 210/198.2 |
| 7,169,299 B2 * | 1/2007 | Iwata et al. | 210/198.2 |
| 7,361,269 B2 * | 4/2008 | Roenneburg et al. | 210/198.2 |
| 2003/0152493 A1 * | 8/2003 | Lefebvre | 422/100 |
| 2003/0165941 A1 * | 9/2003 | Gjerde et al. | 435/6 |
| 2005/0082228 A1 * | 4/2005 | De Lamotte | 210/656 |
| 2005/0161402 A1 * | 7/2005 | Hanafusa et al. | 210/656 |

FOREIGN PATENT DOCUMENTS

| | | |
|---|---|---|
| JP | 2000-19154 | 1/2000 |
| JP | 2001-337079 A | 12/2001 |
| WO | WO-00/12191 A1 | 3/2000 |
| WO | WO-02/062475 A1 | 8/2002 |

\* cited by examiner

FRACTIONATING/COLLECTING DEVICE OF LIQUID CHROMATOGRAPH

CROSS REFERENCE TO RELATED APPLICATIONS

The present application is a Divisional Application of the patent application Ser. No. 10/834,968, filed Apr. 30, 2004, now U.S. Pat. No. 7,138,050, which is based on Priority Documents JP-2003-152611 and JP-2003-152612 filed on May 29, 2003, the entire contents of which are incorporated herein by reference.

BACKGROUND OF THE INVENTION

1. Field of the Invention

The present invention relates to fractionating/collecting devices for fractionating and collecting a separated sample component in a liquid chromatograph, hereinafter also referred to as LC, performing separation analysis of a solution sample.

2. Description of the Related Art

An effluent from a liquid chromatograph is fractionated and collected, and further analyzed in the liquid chromatograph or other analyzing devices such as a mass spectrograph (MS). There a fractionating/collecting device for collecting onto a sample container such as a microplate is used.

One example of the mass spectrograph for analyzing the effluent from the liquid chromatograph is a Matrix Assisted Laser Desorption/Ionization-Time of Flight Mass Spectrometry (MALDI-TOFMS). In the MALDI-TOFMS, when fractionating and collecting sample components separated in the liquid chromatograph on the MALDI-TOFMS analyzing plate using the fractionating/collecting device, the sample components are collected at a number of sites on a single plate. After the collecting process is completed, the plate is manually moved to the MALDI-TOFMS device for analysis.

As only one or two collecting plates can be used in the conventional fractionating/collecting devices, not many analyzing samples can be prepared at night without any workers present, for example, for such MALDI-TOFMS analysis.

Other analyzing methods for analyzing the effluent from the liquid chromatograph includes an LC for performing separation analysis through multiple stages, which include fractionating and collecting the sample component separated in the LC of the first stage with the fractionating/collecting device, and analyzing the collected sample component in the LC of the second stage after processing. In the analysis of protein, for example, in order to further analyze the protein separated in the LC, a digestive enzyme is manually added to the divided and collected sample component of the protein for decomposing to peptide, the peptide being further separated in another LC for analyzing in the MS, and analysis is carried out on the obtained MS data.

In the two-step separation task in the LC, manual tasks such as adding the digestive enzyme take a long time. Therefore, a liquid handler capable of fractionating/collecting and dispensing is used for automatically carrying out the task. Normally in the liquid handler, its probe moves to a fractionating/collecting position of the LC in the first stage to suck in the collected component, and then moves to an injection port in the LC of the second stage to inject the sucked component. Thus, the space in the probe is large, which is disadvantageous especially when a micro LC, for example, is used on the fractionating/collecting side to handle very small amounts of sample.

SUMMARY OF THE INVENTION

The first object of the present invention is to propose a fractionating/collecting device capable of collecting samples on a number of sample containers.

The second object of the present invention is to further propose a fractionating/collecting device capable of shortening time and saving labor in handling the fractionated components between the first and second stages in a LC and which is capable of analyzing a small amount of fractionated component.

The fractionating/collecting device according to the present invention for achieving the first object comprises a fractionating/collecting mechanism for dropping and collecting an effluent from a liquid chromatograph to a sample container from a nozzle, a storage part for storing a number of sample containers, and a carrying mechanism comprising a vertical moving mechanism and a horizontal moving mechanism for both carrying and positioning the sample container to an arbitrary position under the nozzle.

In one aspect of the fractionating/collecting device of the present invention, multiple samples to be analyzed can be prepared since sample collecting can be carried out on a number of sample containers and the sample containers can be stored by providing the storage part for storing a number of sample containers and by configuring the carrying mechanism so as to rotate within a range of the device and to move freely in the vertical and horizontal directions. Furthermore, the carrying mechanism is also used to position the sample container during collecting, and thus the device can be inexpensively realized.

Continuous analysis can also be carried out by combining the conventional fractionating/collecting device and a multipurpose robot arm. However, in comparison with a device of the present invention, such robot arm does not only require to be a two-system robot arm which includes a carrying mechanism for carrying the plate and a collection aiding mechanism for positioning the plate so that a sample liquid is dropped onto an appropriate position on the plate under the nozzle dropping the effluent from the LC, but also requires a large area to install the robot arm.

If the nozzle is configured so that the effluent from the liquid chromatograph and a liquid from another liquid supplying part are simultaneously dropped a matrix liquid, for example, and the effluent from the liquid chromatograph may be simultaneously dropped to form the device for preparing a sample for MALDI-TOFMS exclusively.

If the nozzle is configured so that either the effluent from the liquid chromatograph or a liquid from another liquid supplying part is selectively dropped only the effluent from the liquid chromatograph, for example, may be dropped, and a desired liquid such as matrix liquid or digestive fluid may be subsequently selectively dropped to form a multipurpose sample preparing device.

If the carrying mechanism is configured to be able to carry the sample container, in which sample collecting is completed, to a predetermined position out of the fractionating/collecting device, the sample container can not only be stored within the storage part but can also be automatically loaded to an analyzing device.

If an outlet for discharging gas in the direction of the tip portion of the nozzle is provided at the periphery of the tip portion of the nozzle, it can prevent liquid from remaining at the tip portion of the nozzle.

When a sample fraction dropped onto the plate is dried and crystallized, crystallization will not be even if the moisture content within the collecting device under analyzing process changes. A port for exhausting gas provided in the vicinity of the nozzle can stabilize drying of the fraction.

A fractionating/collecting device of the present invention for achieving the second object comprises a fractionating/collecting mechanism for dropping an effluent from liquid chromatograph to a sample container with a nozzle, a carrying mechanism comprising a vertical moving mechanism and a horizontal moving mechanism for both carrying and positioning the sample container to an arbitrary position under the nozzle, a sample container storage part provided within a movable range of the sample container by the carrying mechanism for storing a number of sample containers, and a suction/injection mechanism provided within a movable range of the sample container by the carrying mechanism for sucking in a sample in the sample container and injecting the sucked sample to another LC.

In another aspect of the present invention, as the fractionating/collecting device comprises a carrying mechanism for carrying and positioning the sample container, and the mechanism for carrying out suction and injection of samples for LC in the next stage within the movable range of the sample container, the LC provided with such fractionating/collecting device can carry out multi-stage chromatograph separation without any manual aid inexpensively and automatically. Furthermore, automatization increases the rate of operation.

As the movable range of the suction/injection mechanism can be restricted by moving the sample container, dead space in the nozzle mechanism of the suction/injection mechanism can be decreased and very small amounts of fraction component can be handled.

The fractionating/collecting device of an open space type (non-closed configuration) has a risk of allowing a condensed water into the sample container when, for example, the sample is being cooled down and thus it is not an ideal condition. If the fractionating/collecting mechanism, the carrying mechanism, the sample container storage part, and the suction/injection mechanism are stored within a sealed space provided with a temperature control mechanism, it is advantageous for preventing condensation when the sample is being cooled down.

If the nozzle for dropping the effluent from the LC is connected to a liquid supplying part for dropping another liquid, for example, an additive liquid such as digestive fluid simultaneously with the drop of the effluent, a device used exclusively for sample preparation to re-separate the fractionated/collected sample can be obtained.

If the nozzle for dropping the effluent from the LC is connected to a liquid supplying part for arbitrary selecting and dropping another liquid at a different timing with the drop of the effluent, a multipurpose sample preparation device for adding an arbitrary additive liquid to the fractionated/collected sample can be obtained.

Other aspects and advantages of the invention will become apparent from the following description, taken in conjunction with the accompanying drawings, illustrating by way of example the principles of the invention.

BRIEF DESCRIPTION OF THE DRAWINGS

The invention, together with aims and advantages thereof, may best be understood by reference to the following description of the presently preferred embodiments together with the accompanying drawings in which.

DETAILED DESCRIPTION OF THE PREFERRED EMBODIMENTS

Figure 1:
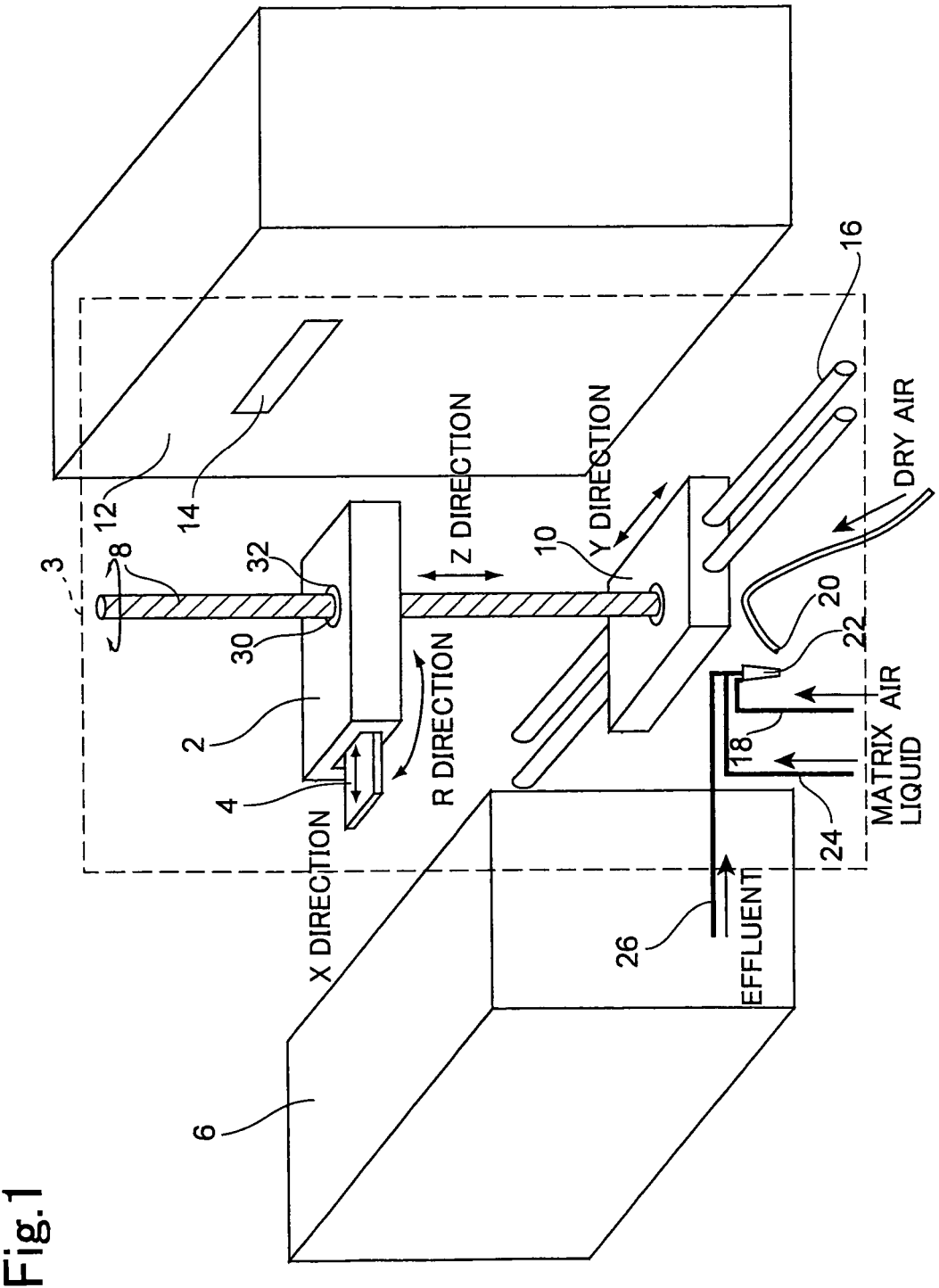
FIG. 1 is a perspective view showing a configuration of one embodiment of the present invention.

FIG. 1 is a schematic diagram showing a preferred embodiment of the present invention.

In FIG. 1, a fractionating/collecting device includes a carrying mechanism 3 arranged next to a mass spectrograph 12 for carrying and positioning a sample container, and a storage part 6 arranged next to the carrying mechanism 3 for storing a number of sample containers. The fractionating/collecting device further includes a nozzle 22 arranged at a position not in the way of the carrying mechanism 3 for discharging a matrix liquid and an effluent from a liquid chromatograph, a port 20 arranged in the vicinity of the nozzle 22 for supplying dry air, and a tube 18 arranged at a periphery of a tip portion of the nozzle 22 for exhausting air in the direction of the tip portion. The tube 18 is connected to a syringe (not shown).

The storage part 6 has shelves for storing a number of sample containers, and is able to store sample containers in which the sample collecting is incomplete and the sample containers in which the sample collecting is complete. The sample containers are, for example, for a MALDI-TOFMS sample plates.

The carrying mechanism 3 includes a holder 4 for holding the sample container, an X-R stage 2 which is provided with a driving mechanism for moving the holder 4 within a plane (X direction), and rotatable (R direction) and movable in the vertical direction (Z direction), a mechanism (not shown) for supporting the X-R stage 2, a rod screw 8 for moving the X-R stage 2 in the vertical direction, a Y stage 10, movable in the Y direction whithin a plane, for supporting the rod screw 8 and a guide 16 for moving the Y stage 10 in the Y direction.

A supporter 30 of the X-R stage 2 has a screw that fits with the rod screw 8. As the rod screw 8 rotates, the X-R stage 2 moves in the vertical direction.

A bearing 32 is provided to the supporter 30, allowing the X-R stage 2 to be maintained in a predetermined direction independently from the rotation of the rod screw 8 and to rotate within the plane.

The Y stage 10 is provided with a mechanism for moving in the Y direction along the guide 16, and a mechanism for rotating the rod screw 8.

The sample container held to be carried by the carrying mechanism 3 can be moved to and positioned at an arbitrary position within the movable range by the moving of the holder 4 in the X direction, the vertical moving as well as the rotation of the X-R stage 2, and the moving of the Y stage 10 in the Y direction.

Figure 2:
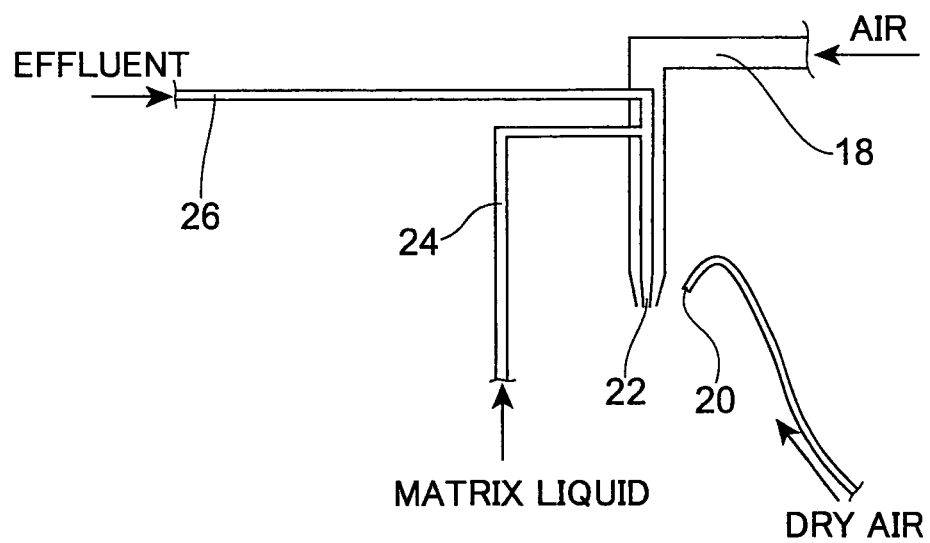
FIG. 2 is a cross sectional view showing a nozzle and mechanisms at the periphery of the nozzle of the embodiment in FIG. 1.

FIG. 2 shows the nozzle 22 for discharging the liquid and mechanisms in the periphery thereof of the above embodiment.

A tube 26 for introducing the effluent from the liquid chromatograph and a tube 24 for introducing the matrix liquid are connected to the nozzle 22. The tube 18 for introducing air is arranged at the periphery of the nozzle 22. Since the nozzle 22 discharges very small amounts of liquid, the liquid sometimes remains at the tip portion of the nozzle 22 due to the surface tension, and can not be satisfactorily dropped onto the sample container. The air exhausted from the periphery of the tip portion of the nozzle 22 then stimulates the liquid to drop.

The port 20 arranged in the vicinity of the nozzle 22 for exhausting dry air blows the dry air to the sample liquid dropped onto the sample container and dries the sample liquid.

The operation of the present embodiment will now be described.

First, the Y stage 10 of the carrying mechanism 3 is moved to a predetermined position of the storage part 6, the rod screw 8 is rotated to move the X-R stage 2 in the Z direction for adjustment of height, the holder 4 is moved in the X direction from the X-R stage 2 to take out the predetermined sample container.

After the sample container is taken out, the carrying mechanism 3 moves the sample container to under the nozzle 22.

Under the nozzle 22, in order to collect the effluent from the liquid chromatograph and the matrix liquid dropped from the nozzle 22 at a predetermined position on the sample container, the carrying mechanism 3 is fine-adjusted in the X and Y directions to be positioned at the liquid drop. After the positioning is finished, the liquid is dropped. The air exhausted from the tube 18 from the air discharging syringe stimulates the liquid dropping.

When the liquid has been dropped, the dry air is blown from the port 20, and the dropped sample liquid is dried and crystallized.

The positioning, dropping and the drying processes are repeatedly carried out until the fractionating/collecting of the relevant sample container is complete.

After fractionating/collecting is completed, the carrying mechanism 3 carries the sample container to the storage part 6 again to store the sample container in the storage part 6. Then the carrying mechanism 3 takes out a new sample container, carries the sample container to under the nozzle 22, and repeats the fractionating/collecting process.

By repeating such processes, a number of sample containers in which fractionating/collecting is complete are stored in the storage part 6.

When analyzing by mass spectrometry, the holder 4 takes out the sample container in which fractionating/collecting is complete from the storage part 6, and the X-R stage 2 rotates over 180 degrees to move the sample container to a loading part 14 of the mass spectrograph 12 for loading.

The sample container in which the sample fractionating/collecting is complete may also be directly loaded from under the nozzle 22 to the mass spectrograph 12.

Figure 3:
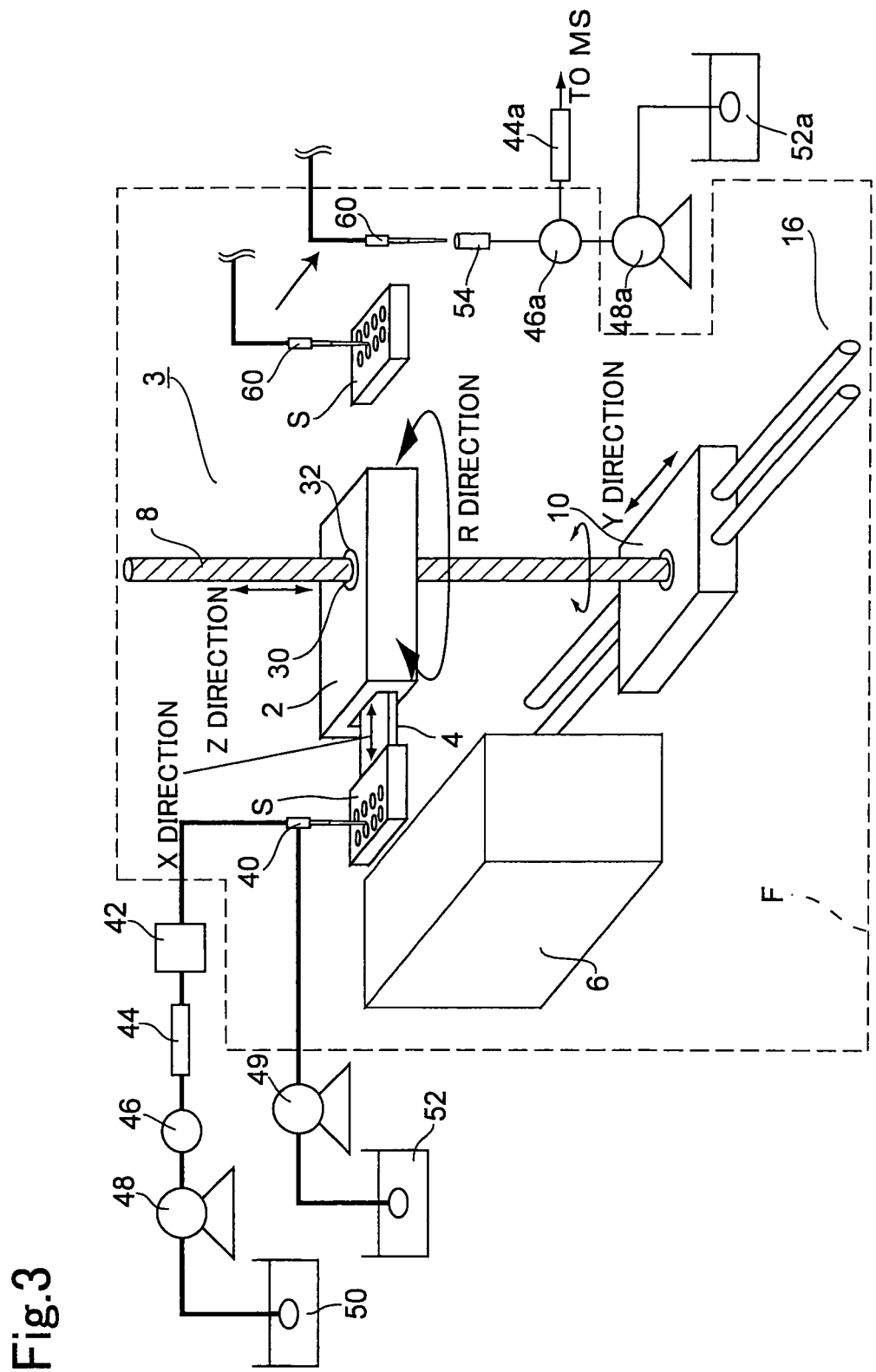
FIG. 3 is a schematic diagram showing a configuration according to another embodiment of the present invention.

FIG. 3 is a schematic diagram showing a configuration of another embodiment.

The fractionating/collecting device of this embodiment is provided with a sample container storage part 6 capable of storing a number of sample containers S such as a microplate, a nozzle 40 for dropping a sample component separated and supplied by the LC and an additive liquid such as digestive fluid supplied from other liquid supplying part to the sample container S, a carrying mechanism 3 for carrying and positioning the sample container S at an arbitrary position under the nozzle 40, and a nozzle 60, which serves as a suction/injection mechanism, for sucking in the fractionated/collected sample component and injecting the sample component to another LC in a housing F shown with a dashed line. The housing F has a temperature control function to maintain its internal space at a predetermined temperature, and has a sealed configuration in which the internal space is externally blocked.

The sample container storage part 6 has shelves for storing a number of sample containers, and both the sample container in which the sample collecting is incomplete and the sample container in which the sample collecting is complete can be stored.

The carrying mechanism 3 is the same as that shown in FIG. 1 and thus the description thereof shall be omitted.

The nozzle 40 is arranged in the vicinity of the carrying mechanism 3 so as not to be in the way of the sample container storage part 6. A tube for sending the effluent from the LC, and a tube for sending an additive liquid 52 such as digestive enzyme or a reactive liquid are connected to the nozzle 40.

In the LC, an eluate 50 is supplied by a pump 48 and sends a sample which is injected from an injector 46, to a column 44. The sample separated in the column 44 is detected in a detector 42 and is dropped from the nozzle 40 and fractionated/collected at the sample container S.

Furthermore, the additive liquid 52 is supplied by a pump 49, and is dropped from the nozzle 40 to the sample container S. The additive liquid 52 can be dropped onto the sample container S simultaneously with the effluent from the LC by having the pump 49 continuously supplied the liquid, or can be dropped after the effluent from the LC is dropped by having the pump 49 supplied the liquid over a predetermined time.

The nozzle 60 is arranged within a movable range of the sample container S at a position different from the nozzle 40. In this embodiment, the nozzle 60 is arranged on the side opposite the nozzle 40 with respect to the carrying mechanism 3. The nozzle 60 is movably supported so as to be able to suck in the sample in the sample container S and inject the sucked sample into an injection port 54 placed within the housing F.

The injection port 54 is connected to an injector 46a of the LC of the next stage, and injects the sample to the LC of the next stage by way of the injector 46a. In the LC of the next stage, the eluate 52a is supplied by a pump 48a, and sends the sample, which is injected from the injector 46a, to a column 44a. The sample component separated in the column 44a is supplied to the MS, which is acting as a detector, to be detected.

The operation of the present embodiment shall now be described.

First, the carrying mechanism 3 moves to the position of the sample container storage part 6, and the holder 4 moves in the X direction to take out the sample container S. The sample container S taken out is carried to under the nozzle 40, and the effluent from the LC and the additive liquid 52 such as digestive enzyme are dropped thereon from the nozzle 40. The collecting task is carried out by positioning the sample container in the X and Y directions by means of the carrying mechanism 3 so that the effluent 50 and the additive liquid 52 are dropped to an appropriate location on the sample container S.

The sample container S, in which the sample collecting is complete, is stored in the sample container storage part 6, a new sample container S is taken out from the sample container storage part 6, and the collecting of the new sample is repeated. In the sample container storage part 6, the collected samples are maintained at a constant temperature.

The sample container S completed with sample collecting and stored in the sample container storage part 6 is taken out as needed from the sample container storage part 6 by means of the carrying mechanism 3. Then the X-R stage 2 is rotated over 180 degrees with the rod screw 8 as the center and is further adjusted in height to position the sample container S under the nozzle 60. The nozzle 60 sucks in the sample in the sample container S, moves to the injection port 54 placed nearby and injects the sucked sample to the injection port 54.

The sample injected to the injection port 54 is sent to the column 44*a* with the eluate 52*a* supplied by the pump 48*a* from the injector 46*a*, and is further separated and sent to the MS for detection.

What is claimed is:

1. A fractionating/collecting device comprising:
   a fractioning/collecting mechanism for dropping and collecting an effluent from liquid chromatograph onto a sample container with a nozzle;
   a storage part for storing a number of sample containers; and
   a carrying mechanism having a vertical shaft provided with a vertical moving mechanism and a horizontal moving mechanism to carry and position the sample container at an arbitrary position under the nozzle,
   wherein the horizontal moving mechanism comprises an X-R stage for moving the sample container in the radius direction from the shaft within a plane, being rotatable in the circumferential direction around the shaft, and a Y stage for moving the shaft in the Y direction within the plane, and
   wherein the vertical moving mechanism moves the X-R stage in the vertical direction along the shaft.

2. The fractioning/collecting device according to claim 1, wherein the horizontal moving mechanism is configured to move the sample container to a determined position out of the fractioning/collecting device.

3. The fractioning/collecting device according to claim 1, wherein the nozzle is configured so as to simultaneously drop the effluent from the liquid chromatograph and a liquid from another liquid supplying part.

4. The fractioning/collecting device according to claim 1, wherein the nozzle is configured so as to selectively drop one of either the effluent from the liquid chromatograph or a liquid from another liquid supplying part.

5. The fractioning/collecting device according to claim 1, wherein an outlet for blowing gas in a direction of the tip portion of the nozzle is provided at a periphery of a tip portion of the nozzle.

6. The fractioning/collecting device according to claim 1, wherein a port for exhausting gas is arranged in the vicinity of the nozzle, the exhausted gas drying the collected sample.

* * * * *